United States Patent [19]
Calvo et al.

[11] Patent Number: 5,143,723
[45] Date of Patent: Sep. 1, 1992

[54] COLORED COSMETIC COMPOSITIONS

[75] Inventors: Luis C. Calvo, Bayshore; David W. Peters, Amityville, both of N.Y.

[73] Assignee: Estee Lauder, Inc., New York, N.Y.

[21] Appl. No.: 485,963

[22] Filed: Mar. 5, 1990

Related U.S. Application Data

[63] Continuation-in-part of Ser. No. 275,434, Nov. 23, 1988, abandoned.

[51] Int. Cl.$^5$ .................... A61K 7/021; A61K 7/025; A61K 7/043; A61K 7/13
[52] U.S. Cl. ........................................ 424/63; 424/64; 424/61; 424/69; 424/70; 424/78.03; 424/401; 8/506; 106/499; 514/844
[58] Field of Search .................... 424/63, 64, 69, 61, 424/81, 78, 82-83; 8/506, 508-510, 512-516, 519, 520; 106/493, 499; 252/301.34, 301.35

[56] References Cited

U.S. PATENT DOCUMENTS

| | | | |
|---|---|---|---|
| Re. 25,845 | 8/1965 | D'Alelio et al. | 252/301.2 |
| 2,498,592 | 2/1950 | Switzer et al. | 428/409 X |
| 2,498,593 | 2/1950 | Switzer et al. | 252/301.2 |
| 2,649,382 | 8/1953 | Vesce | 424/64 |
| 2,851,424 | 9/1958 | Switzer et al. | 428/436 X |
| 2,938,873 | 5/1960 | Kazenas | 252/301.35 |
| 3,177,272 | 4/1965 | Plymale | 264/75 |
| 3,196,079 | 7/1965 | Blaustein et al. | 167/92 |
| 3,211,619 | 10/1965 | Buchwalter et al. | 167/85 |
| 3,275,715 | 9/1966 | O'Leary, Jr. | 260/889 |
| 3,361,677 | 1/1968 | Voedisch | 252/301.2 |
| 3,409,585 | 11/1968 | Hagemeyer et al. | 260/41 |
| 3,412,034 | 11/1968 | McIntosh et al. | 252/301.2 |
| 3,449,291 | 6/1969 | Lerman et al. | 260/41 |
| 3,467,642 | 9/1969 | Horiguchi et al. | 260/141 |
| 3,518,205 | 6/1970 | Vukasovich | 252/301.3 |
| 3,786,018 | 1/1974 | Nadler | 260/32.6 |
| 3,856,550 | 12/1974 | Bens et al. | 117/33.5 |
| 3,873,687 | 3/1975 | Demko | 424/64 |
| 3,988,437 | 10/1976 | Bradner | 424/59 |
| 4,309,411 | 1/1982 | Toida et al. | 424/63 |
| 4,323,554 | 4/1982 | Bernhard | 424/63 |
| 4,438,140 | 3/1984 | Guillon et al. | 424/64 X |
| 4,533,484 | 8/1985 | Walles et al. | 252/117 |
| 4,710,375 | 12/1987 | Talcasuka et al. | 424/69 |
| 4,732,570 | 3/1988 | Baumgartner et al. | 8/506 |
| 4,772,331 | 9/1988 | Noguchi et al. | 106/417 |
| 4,801,445 | 1/1989 | Fukui et al. | 424/69 |

FOREIGN PATENT DOCUMENTS

| | | |
|---|---|---|
| 562729 | 9/1958 | Canada . |
| 0195575 | 3/1986 | European Pat. Off. . |
| 770889 | 1/1952 | United Kingdom . |
| 733856 | 7/1955 | United Kingdom . |
| 820111 | 3/1956 | United Kingdom . |

OTHER PUBLICATIONS

Moxey, "Colors-Not So Pure and Simple" vol. 53, No. 10 Oct. 1982 Manufacturing Chemist pp. 46, 47 and 49.
Carson "Recon Offers Polymer Entrapment for Nail Polish" HAPPI, vol. 23, No. 8 Aug. 1986 pp. 54-55.

*Primary Examiner*—Thurman K. Page
*Assistant Examiner*—James M. Spear
*Attorney, Agent, or Firm*—Philippe Y. Riesen

[57] ABSTRACT

Disclosed are colored cosmetic compositions that, when applied to a person's skin (e.g., the lips or cheeks), hair or nails, exhibit exceptional brilliance and clarity of color, and a method of using those compositions to provide an aesthetically pleasing appearance to the skin, hair or nails. The compositions comprise: (a) a pigment formed by incorporating a solvated dye into a resin, and (b) a cosmetic carrier having admixed therein the pigment in an amount effective to provide an attractive cosmetic effect to the composition when it is applied to a person's skin, hair, or nails. The methods of this invention comprise applying an effective amount of the foregoing composition to a person's skin (e.g., lips or cheeks), hair or nails.

35 Claims, No Drawings

COLORED COSMETIC COMPOSITIONS

RELATED APPLICATION

This application is a continuation-in-part of our earlier filed application Ser. No. 275,434, filed Nov. 23, 1988, now abandoned.

TECHNICAL FIELD OF THE INVENTION

This invention relates to colored cosmetic compositions. More particularly, this invention relates to cosmetic compositions that, when applied to a person's skin (e.g., the lips or cheeks), hair or nails, exhibit exceptional brilliance and clarity of color, and a method of using those compositions to provide an aesthetically pleasing appearance to the skin, hair or nails.

BACKGROUND OF THE ART

The use of cosmetics is widespread in modern society. Cosmetics typically are intended to provide an attractive appearance through the use of color, e.g., by highlighting certain features of the face and/or accentuating natural colors. Colored cosmetics are used, for example, to accentuate lines of separation (eye liners and lip liners), to provide sensuous color to portions of the skin (lipsticks and glosses) and to provide a "healthy glow" to the cheeks (blushes and rouges). Cosmetics may also be used to hide imperfections of the skin and to protect the skin (e.g., by blocking the skin from harmful ultraviolet light).

A variety of coloring agents can be used to color cosmetics, including inorganic and organic dyes or pigments. Generally, to be useful as cosmetic colorants, soluble dyes must be converted into insoluble forms. For the purposes of this application, any soluble dye that is in solution, will be referred to as a "solvated dye". A solvated dye composed of a water-soluble dye in an aqueous solution will be referred to as an "aqueous dye". A "pigment" is any soluble dye, whether in a dry, powder form, or in solution, that has been converted into an insoluble form. There are a variety of methods currently used in the cosmetic industry to insolubilize soluble dyes. The most common method used to insolubilize water-soluble dyes is called "laking". "Lake" colorants are metallic complexes of organic coloring matter obtained by precipitating an organic dyestuff onto an inorganic substrate. See generally U.S. Pat. No. 3,873,687. Water-soluble dyes have also been insolubilized by salifying the dyes with copolymers. See generally U.S. Pat. No. 4438,140.

Applicants have discovered that cosmetics containing pigments formed by incorporating a solvated dye into a resin, exhibit superior brilliance and clarity of color, as compared to cosmetics containing pigments formed through conventional processes, such as, e.g., "laking". Thus, the pigments used in the compositions of this invention typically are made by incorporating a solvated dye into a resin to obtain a colored resin, which then may be ground into a powdered pigment suitable for cosmetic applications.

Any soluble dye can be used to manufacture the pigments used in the compositions of this invention. The preferred dyes used to manufacture the pigments used in the compositions of this invention are water-soluble dyes. For example, several different methods for the manufacture of these pigments using daylight fluorescent dyes are described generally in U.S. Pat. Nos. 2,938,873 and 2,498,592.

To the best of our knowledge, to date the pigments used in the compositions of this invention have not been utilized in cosmetic compositions. Neither, to the best of our knowledge, have these pigments been applied to the skin (e.g., the lips or cheeks), hair, or nails to enhance their appearance.

It is an object of the present invention to provide cosmetic compositions that are characterized by their exceptional brilliance and clarity of color.

A further object of this invention is to provide attractive colored cosmetic compositions that are stable and safe for application to the human skin, hair, or nails.

Another object of this invention is to provide a method of providing an attractive appearance to the skin, hair, or nails.

SUMMARY OF THE INVENTION

The present invention relates to compositions and methods for achieving the foregoing objects. The compositions comprise:

(a) a pigment formed by incorporating a solvated dye into a resin, and (b) a cosmetic carrier having admixed therein the pigment in an amount effective to provide an attractive cosmetic effect to the composition when it is applied to a person's skin, hair or nails. The methods of this invention comprise applying an effective amount of the foregoing composition to a person's skin (e.g., lips or cheeks), hair or nails.

The pigment component of the compositions of this invention should be present in an amount sufficient to provide the skin, hair, or nails with an aesthetically pleasing effect. Preferably the pigment comprises about 0.5%–50% by weight of the composition. The solvated dye preferably comprises about 0.1%–50% by weight of the pigment.

The compositions of this invention may take a wide variety of forms, e.g., lipsticks, glosses, blush powders and mascaras and other similar make-up compositions. The cosmetic carrier may comprise a wide variety of ingredients that are conventionally used in cosmetics, e.g., waxes, mineral oils, fatty alcohols, glycerine, and sunscreens.

DETAILED DISCLOSURE OF THE INVENTION

Any soluble dye may be used to make the compositions of this invention, provided it is safe for application to the skin, hair or nails, has a desirable color and is compatible with the other components of the composition. It is desireable to use a dye that it is approved for drug and cosmetic use (D&C dyes) or food, drug and cosmetic use (FD&C dyes). The preferred dyes for use in the compositions of this invention are water-soluble dyes, and include FD&C Blue No. 1, FD&C Blue No. 2, FD&C Green No. 3, FD&C Red No. 3, FD&C Red No. 40, FD&C Yellow No. 5, FD&C Yellow No. 6, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Orange No. 17, FD&C Red No. 4, D&C Red No. 6, D&C Red No. 7, D&C Red No. 8, D&C Red No. 9, D&C Red No. 17, D&C Red No. 19, D&C Red No. 21, D&C Red No. 22, D&C Red No. 27, D&C Red No. 28, D&C Red No. 30, D&C Red No. 31, D&C Red No. 34, D&C Red No. 39, FD&C Red No. 40, D&C Violet No. 2, D&C Yellow No. 7, Ext. D&C Yellow No. 7, D&C Yellow No. 8, D&C Yellow No. 11, D&C Brown No. 1, Ext. D&C Violet No. 2, D&C Blue No. 6 and D&C Yellow No. 10. Such dyes are well known, commercially available materials, with their chemical structure being described, e.g., in 21 C.F.R. Part 74 (as revised Apr. 1, 1988) and the *CTFA Cosmetic Ingredient Handbook*, (1988), published by the Cosmetics, Toiletry and Fragrancy Association, Inc. These publications are incorporated herein by reference.

Any resin may be used in the compositions of this invention, provided it can be pulverized to a fine powder, is safe for application to the skin, and is compatible with the other components of the composition. The resin may be thermoplastic or thermosetting. The use of thermosetting materials is generally advantageous because such materials are more readily ground to minute pigment-size particles, without tending to "gum-up" or agglomerate during grinding.

Preferred resins are those that do not absorb appreciable amounts of light. Preferably, the resins are transparent or at least translucent.

Polymeric materials approved by the Food and Drug Administration as "Indirect Food Additives" are especially preferred resins for use in the make-up compositions of this invention. These materials are well known, commercially available materials, described in 21 C.F.R. Part 177 (as revised Apr. 11, 1988), which publication is incorporated herein by reference, and include, acrylic and modified acrylic plastics; acrylonitrile/-butadiene/styrene copolymers; acrylonitrile/-butadiene/styrene/methyl methacrylate copolymers; acrylonitrile/styrene copolymers; acrylonitrile/styrene copolymers modified with butadiene/styrene elastomer; cellophane; cyclohexylene dimethylene terephthalate and 1,4-cyclohexylene dimethylene isophthalate copolymers; ethylene-acrylic acid copolymers; ethylene-1,4-cyclohexylene dimethylene terephthalate copolymers; ethylene-ethyl acrylate copolymers; ionomeric resins; ethylene-methyl acrylate copolymer resins; ethylene-vinyl acetate copolymers; ethylene-vinyl acetate-vinyl alcohol copolymers; fluorocarbon resins; hydroxyethyl cellulose film, water-insoluble; isobutylene polymers; isobutylenebutene copolymers; 4,4'-isopropylidenediphenolepichlorohydrin resins; melamine-formaldehyde resins; nitrile rubber modified acrylonitrile-methyl acrylate copolymers; nylon resins; olefin polymers; perfluorocarbon resins; polyarylate resins; polyarylsulfone resins; poly-1-butene resins and butene/ethylene copolymers; polycarbonate resins; polyester elastomers; polyetherimide resins; polyethylene resins, carboxyl modified; polyethylene, chlorinated; polyethylene, fluorinated; polyethylene, oxidized; polyethylene phthalate polymers; poly(p-methylstyrene) and rubber-modified poly(p-methylstyrene); polystyrene and rubber-modified polystyrene; polysulfide polymer-polyepoxy resins; polysulfone resins; poly(tetramethylene terephthalate); polyvinyl alcohol films; polyurethane resins; styrene block polymers; styrene-maleic anhydride copolymers; styrene-methyl methacrylate copolymers; textryls; urea-formaldehyde resins; vinyl chloride-ethylene copolymers; vinyl chloride-hexene-1 copolymers; vinyl chloride-lauryl vinyl ether copolymers; vinyl chloride-propylene copolymers; vinylidene chloride/methyl acrylate copolymers; vinylidene chloride/methyl acrylate/methyl methacrylate polymers; ethylene polymers, chlorosulfonated; 4,4'-isopropylidenediphenol-epichlorohydrin thermosetting epoxy resins; mineral reinforced nylon resins; perflourocarbon cured elastomers; phenolic resins; polyester resins, cross-linked; polyether resins, chlorinated; polyethersulfone resins; polyamide-imide resins; poly(2,6-dimethyl-1,4-phenylene) oxide resins; polyoxymethylene copolymers; polyoxymethylene homopolymers; polyphenylene sulfide resins; polyvinylidene fluoride resins; and styrene-divinylbenzene resins, cross-linked.

The pigments used in the compositions of this invention are formed by the incorporation of a solvated dye into the resin, with the resultant coloring of the resin. Without wishing to be bound by any theory, it is believed that the solvated dye is absorbed into, encapsulated, enveloped or entrapped by the resin, dispersed throughout the resin, or dissolved in the resin, depending on the particular dyes and resins used and the method used to incorporate the dye into the resin. Accordingly, for the purposes of this application, "incorporate" or "incorporation" are general terms used to describe the coloring of a resin by a solvated dye, and is meant to encompass the dispersion, entrapment, encapsulation, envelopment, dissolution etc., of the solvated dye in the resin, with resultant coloration of the resin.

Regardless of the particular method used to incorporate the solvated dye into the resin, applicants have discovered that when a soluble dye is dissolved into solution and the solution is incorporated into a resin and the resulting pigment is admixed with a cosmetic carrier, the resulting cosmetic composition exhibits exceptional clarity and brilliance of color.

The coloring of the resin with the solvated dye can be accomplished by conventional techniques such as those employed to incorporate other additives into such resins. For example, the resin may be colored by simply adding a solvated dye to the resin while the resin is in a plasticized or molten state (e.g., during the manufacture of the resin, or by heating the already formed resin above its melting point), under appropriate temperature and pressure conditions. A technique for incorporating a dye in aqueous solution into a resin by dissolving the dye in a solution of unpolymerized resin and a mutual solvent for the resin and dye, followed by the polymerization of the resin, is described in U.S. Pat. No. 2,498,592. The resin may also be colored by contacting dry, powdered resin with a solvated dye. See generally U.S. Pat. Nos. 2,498,592 and 2,938,873.

The resulting pigment, regardless of how it is made, may be pulverized. If pulverization does not result in a powder having the desired particle size distribution, the average size of the pigment particles may be narrowed by any of various systems of classification, (e.g., by sieving or by air classification.) Preferably, the pigment particles are substantially uniform in size and do not exceed about 100 or 150 microns in diameter. Very fine particle sizes in the range of about 5–25 microns are most satisfactory for use in the invention, although larger and smaller particle sizes may be used.

Depending on the color effect desired, and their physical compatibility, any mixture of solvated dyes may be used in the compositions of this invention. Also depending on the color effect desired, one or more dyes or pigments other than solvated dyes may also be included in the compositions of this invention. Virtually all (if not all) of the coloring materials that are currently being used in commercial cosmetic compositions are suitable for such use. Among such materials are the lake of D&C Red #3, D&C Red #6, D&C Red #7, the lake of D&C Red #21, the lake of D&C Red #27, D&C Red #30, D&C Red #33, D&C Red #36, the lake of D&C Red #40, the lake of FD&C Yellow #6, D&C Yellow #6, the lake of D&C Yellow #10, the lake of FD&C Blue #1, and the lake of D&C Blue #1. Additionally, any of the colorants listed in Subparts A-C of 21 C.F.R. Part 73 (as revised Apr. 1, 1988), which publication is incorporated herein by reference, may be included in the compositions of this invention.

While the compositions of this invention may be applied to any portion of the skin, hair or nails, in the most preferred embodiments the compositions are applied to the cheeks or to the lips. The compositions, therefore, preferably take a form suitable for such applications, e.g., the form of a lipstick or a powder for application to the cheeks.

The cosmetic carrier for the pigments used in the compositions of this invention is chosen to provide a composition that has the desired form (e.g., a lipstick or a powder). The cosmetic carrier should, of course, also be compatible with the pigments and be suitable for application to the skin, hair, or nails of a person.

Suitable cosmetic carriers are well known in the cosmetic art and include a vast array of materials. For example:

(1) When the composition takes the form of stick (e.g., a lipstick), at least a portion of the carrier typically will be a wax. Suitable waxes may be selected from the group consisting of lanolin, beeswax, candelilla wax, carnauba wax, cocoa butter, silicone waxes, fatty acids having a chain length of C12-C22, salts of the foregoing fatty acids, and mixtures thereof. In addition, the carrier may also include one or more oils, such as oils selected from the group consisting of paraffin oil, purcellin oil, sweet almond oil, avocado oil, castor oil, sesame oil, jojoba oil, mineral oils, silicone oils, cereal-germ oils, and mixtures thereof. The carrier may also include any number of colorants, flavorings or perfumes that are conventionally used in lipsticks.

(2) When the composition takes the form of a powder (e.g., a rouge composition for application to the cheeks), the carrier typically will comprise a mineral or organic filler, such as materials selected from the group consisting of talc, kaolin, starch, polyethylene powder, polyamide powder and mixtures thereof. The carrier may also include other materials that are conventionally used in many commercial cosmetic powders such as binders and colorants.

(3) When the composition takes the form of a liquid, the carrier typically comprises a mixture of one or more waxes and one or more oils. The same waxes and oils that may be used to make the lipsticks of this invention may also be used to make products of the invention that are in liquid forms, except that the specific oil and wax components and the amounts of those components are selected to provide a product that is in a liquid form, as opposed to a stick, at room temperature.

Regardless of the form of the product, the compositions of this invention may also include one or more ingredients that are conventionally used in cosmetic compositions Such ingredients include, for example, perfumes; sunscreens, such as paraaminobenzoic acid (PABA) and its derivatives; anti-oxidants, such as butylated hydroxyanisole, butylated hydroxytoluene, tocopherol and ascorbyl palmitate; and preservatives, such as butyl paraben and ethyl paraben.

In addition to protecting the skin from the harmful effects of ultraviolet light, sunscreens such as PABA perform the additional function of diminishing the harmful degradative effects of such light on the pigments and colorants in the compositions, which can cause such pigments and colorants to fade over time. Other ultraviolet absorbers that are not conventionally classified as sunscreens, such as titanium dioxide, may also be included in the compositions of this invention for the purpose of diminishing the harmful degradative effects of ultraviolet light on the pigments and colorants in the compositions.

The pigments and cosmetic carriers may be combined to prepare the compositions of this invention by techniques currently used to prepare cosmetic compositions.

The following examples illustrate the invention, but are not to be construed as limiting the invention which is defined in the claims appended hereto.

EXAMPLE I

This example illustrates a procedure for making a pigment used in the compositions of this invention from the following ingredients: deionized water, sodium octoxynol-2 ethane sulfonate (TRITON X200, Rohm & Haas Co.), glacial acetic acid, FD&C Blue #1 and powdered toluene sulfonamide formaldehyde resin (SANTOLITE, Monsanto Corp.).

Procedure

We dissolved 3 grams of TRITON X200 (a wetting agent that facilitates dye penetration) and 30 grams of glacial acetic acid into 120 grams of deionized water. We added 0.3 gram of FD&C Blue #1 to the solution, and mixed it for 10 minutes using a suitable laboratory mixer at a low speed, e.g, 30 rpms. We then added 15.0 grams of the powdered toluene sulfonamide formaldehyde resin and mixed the slurry for three additional minutes at the same speed.

The excess water was then decanted and the remaining pigment washed 8 times with deionized water. After the final decanting, the pigment was dried and pulverized using a mortar and pestle.

All these operations took place at room temperature.

EXAMPLE II

This example illustrates a procedure for making a pigment used in the compositions of this invention from a fluorescent dye (D&C Yellow #8 dye), and the following ingredients: deionized water, sodium octoxynol-2 ethane sulfonate (TRITON X200, Rohm & Haas Co.), glacial acetic acid and powdered toluene sulfonamide formaldehyde resin (SANTOLITE, Monsanto Corp.).

Procedure

We dissolved 3 grams of TRITON X200 (a wetting agent that facilitates dye penetration) and 30 grams of glacial acetic acid into 120 grams of deionized water. We added 0.3 gram of D&C Yellow #8 to the solution, and mixed it for 10 minutes using a suitable laboratory mixer at a low speed, e.g, 30 rpms. We then added 15.0 grams of the powdered toluene sulfonamide formaldehyde resin and mixed the slurry for three additional minutes at the same speed.

The excess water was then decanted and the remaining pigment washed 8 times with deionized water. After the final decanting, the pigment was dried and pulverized using a mortar and pestle.

All these operations took place at room temperature.

EXAMPLE III

This example illustrates a procedure for making a lipstick composition containing the pigments used in the compositions of this invention from the following ingredients: castor oil, candelilla, carnauba, castor wax, beeswax, ozokerite, lanolin, lanolin oil, mineral oil, butyl stearate and the Example II pigment.

Procedure 41.00 grams of castor oil, 7.80 grams of candelilla, 2.00 grams of carnauba, 0.60 grams of castor wax, 2.40 grams of beeswax, 3.60 grams of ozokerite, 7.80 grams of lanolin, 7.80 grams of lanolin oil, 3.00 grams of mineral oil, and 9.00 grams of butyl stearate were combined, heated to 80° C. and mixed gently until homogeneous. 3.00 grams of the Example II pigment was then added to 12.00 grams of castor oil and ground 3 times through a roller mill. This was added to the oil/wax mixture, which was then mixed until homogeneous, cooled to 60° C. and poured into lipstick molds. The resulting sticks were cooled, withdrawn from the molds and fitted into lipstick cases.

EXAMPLE IV

This example illustrates a procedure for making a pressed powder blush containing a pigment used in the compositions of this invention from the following ingredients: talc, zinc stearate, mica, the Example II pigment, cetyl alcohol, mineral oil (70 cps), and octyl dodecanol (STANDAMUL G, Henkel).

Procedure 66.0 grams of talc, 2.0 grams of zinc stearate, 6.0 grams of mica and 20.0 grams of the Example II pigment were blended together and pulverized to yield a finely divided powder.

1.2 grams of cetyl alcohol, 1.2 grams of mineral oil and 3.6 grams of octyl dodecanol were combined, heated to 65° C. and mixed gently until homogeneous. The resulting mixture was then sprayed over the above-described powder. This was then blended until uniform in a ribbon blender.

We claim:

1. A cosmetic composition comprising: (a) a pigment formed by incorporating a solvated dye into a resin that is transparent to light and acts as a solvent for the dye, the pigment being ground to a particle size of about 5-150 microns that is suitable for use in a cosmetic composition, and (b a cosmetic carrier having admixed therein said pigment in an amount of about 0.5%-50% by weight of the composition, effective to provide an attractive cosmetic effect to the composition when it is applied to a person's skin, hair or nails.

2. The composition according to claim 1, wherein the solvated dye is an aqueous dye.

3. The composition according to claim 1, wherein the solvated dye is incorporated into the resin by adding the dye to the resin while the resin is in a plasticized or molten state.

4. The composition according to claim 1, wherein the solvated dye is incorporated into the resin by dissolving the dye in a solution of unpolymerized resin and a mutual solvent for the resin and the dye, followed by the polymerization of the resin.

5. The composition according to claim 1, wherein the solvated dye is incorporated into the resin by contacting the dye with the resin.

6. The composition according to claim 1, wherein the solvated dye is an aqueous solution of any dye selected from the group consisting of FD&C Blue No. 1, FD&C Blue No. 2, FD&C Green No. 3, FD&C Red No. 3, FD&C Red No. 40, FD&C Yellow No. 5, FD&C Yellow No. 6, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Orange No. 17, FD&C Red No. 4, D&C Red No. 6, D&C Red No. 7, D&C Red No. 8, D&C Red No. 9, D&C Red No. 17, D&C Red No. 19, D&C Red No. 21, D&C Red No. 22, D&C Red No. 27, D&C Red No. 28, D&C Red No. 30, D&C Red No. 31, D&C Red No. 34, D&C Red No. 39, FD&C Red No. 40, D&C Violet No. 2, D&C Yellow No. 7, Ext. D&C Yellow No. 7, D&C Yellow No. 8, D&C Yellow No. 11, D&C Brown No. 1, Ext. D&C Violet No. 2, D&C Blue No. 6 and D&C Yellow No. 10.

7. The composition according to claim 3, wherein the solvated dye is an aqueous solution of any dye selected from the group consisting of FD&C Blue No. 1, FD&C Blue No. 2, FD&C Green No. 3, FD&C Red No. 3, FD&C Red No. 40, FD&C Yellow No. 5, FD&C Yellow No. 6, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Orange No. 17, FD&C Red No. 4, D&C Red No. 6, D&C Red No. 7, D&C Red No. 8, D&C Red No. 9, D&C Red No. 17, D&C Red No. 19, D&C Red No. 21, D&C Red No. 22, D&C Red No. 27, D&C Red No. 28, D&C Red No. 30, D&C Red No. 31, D&C Red No. 34, D&C Red No. 39, FD&C Red No. 40, D&C Violet No. 2, D&C Yellow No. 7, Ext. D&C Yellow No. 7, D&C Yellow No. 8, D&C Yellow No. 11, D&C Brown No. 1, Ext. D&C Violet No. 2, D&C Blue No. 6 and D&C Yellow No. 10.

8. The composition according to claim 4, wherein the solvated dye is an aqueous solution of any dye selected from the group consisting of FD&C Blue No. 1, FD&C Blue No. 2, FD&C Green No. 3, FD&C Red No. 3, FD&C Red No. 40, FD&C Yellow No. 5, FD&C Yellow No. 6, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Orange No. 17, FD&C Red No. 4, D&C Red No. 6, D&C Red No. 7, D&C Red No. 8, D&C Red No. 9, D&C Red No. 17, D&C Red No. 19, D&C Red No. 21, D&C Red No. 22, D&C Red No. 27, D&C Red No. 28, D&C Red No. 30, D&C Red No. 31, D&C Red No. 34, D&C Red No. 39, FD&C Red No. 40, D&C Violet No. 2, D&C Yellow No. 7, Ext. D&C Yellow No. 7, D&C Yellow No. 8, D&C Yellow No. 11, D&C Brown No. 1, Ext. D&C Violet No. 2, D&C Blue No. 6 and D&C Yellow No. 10.

9. The composition according to claim 5, wherein the solvated dye is an aqueous solution of any dye selected from the group consisting of FD&C Blue No. 1, FD&C Blue No. 2, FD&C Green No. 3, FD&C Red No. 3, FD&C Red No. 40, FD&C Yellow No. 5, FD&C Yellow No. 6, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Orange No. 17, FD&C Red No. 4, D&C Red No. 6, D&C Red No. 7, D&C Red No. 8, D&C Red No. 9, D&C Red No. 17, D&C Red No. 19, D&C Red No. 21, D&C Red No. 22, D&C Red No. 27, D&C Red No. 28, D&C Red No. 30, D&C Red No. 31, D&C Red No. 34, D&C Red No. 39, FD&C Red No. 40, D&C Violet No. 2, D&C Yellow No. 7, Ext. D&C Yellow No. 7, D&C Yellow No. 8, D&C Yellow No. 11, D&C Brown No. 1, Ext. D&C Violet No. 2, D&C Blue No. 6 and D&C Yellow No. 10.

10. The composition according to claim 1, wherein the resin is a polymeric material selected from the group consisting of acrylic and modified acrylic plastics; acrylonitrile/butadiene/styrene copolymers; acrylonitrile/butadiene/styrene/methyl methacrylate copolymers; acrylonitrile/styrene copolymers; acrylonitrile/styrene copolymers modified with butadiene/styrene elastomer; cellophane; cyclohexylene dimethylene terephthalate and 1,4-cyclohexylene dimethylene isophthalate copolymers; ethylene-acrylic acid copolymers; ethylene-1,4-cyclohexylene dimethylene terephthalate copolymers; ethylene-ethyl acrylate copolymers; ionomeric resins; ethylene-methyl acrylate copolymer resins; ethylene-vinyl acetate copolymers; ethylene-vinyl acetate-vinyl alcohol copolymers; fluorocarbon resins; hydroxyethyl cellulose film, water-insoluble; isobutylene polymers; isobutylenebutene copolymers; 4,4'-isopropylidenediphenolepichlorohydrin resins; melamine-formaldehyde resins; nitrile rubber modified acrylonitrile-methyl acrylate copolymers; nylon resins; olefin polymers; perfluorocarbon resins; polyarylate resins; polyarylsulfone resins; poly-1-butene resins and butene/ethylene copolymers; polycarbonate resins; polyester elastomers; polyetherimide resins; polyethylene resins, carboxyl modified; polyethylene, chlorinated; polyethylene, fluorinated; polyethylene, oxidized; polyethylene phthalate polymers; poly(p-methylstyrene) and rubber-modified poly(p-methylstyrene); polystyrene and rubber-modified polystyrene; polysulfide polymer-polyepoxy resins; polysulfone resins; poly (tetramethylene terephthalate); polyvinyl alcohol films; polyurethane resins; styrene block polymers; styrene-maleic anhydride copolymers; styrene-methyl methacrylate copolymers; textryls; urea-formaldehyde resins; vinyl chloride-ethylene copolymers; vinyl chloride-hexene-1 copolymers; vinyl chloride-lauryl vinyl ether copolymers; vinyl chloride-propylene copolymers; vinylidene chloride/methyl acrylate copolymers; vinylidene chloride/methyl acrylate/methyl methacrylate polymers; ethylene polymers, chlorosulfonated; 4,4'-isopropylidenediphenol-epichlorohydrin thermosetting epoxy resins; mineral reinforced nylon resins; perflourocarbon cured elastomers; phenolic resins; polyester resins, cross-linked; polyether resins, chlorinated; polyethersulfone resins; polyamide-imide resins; poly(2,6-dimethyl-1,4-phenylene) oxide resins; polyoxymethylene copolymers; polyoxymethylene homopolymers; polyphenylene sulfide resins; polyvinylidene fluoride resins; and styrenedivinylbenzene resins, cross-linked.

11. The composition according to claim 3, wherein the resin is a polymeric material selected from the group consisting of acrylic and modified acrylic plastics; acrylonitrile/butadiene/styrene copolymers; acrylonitrile/butadiene/styrene/methyl methacrylate copolymers; acrylonitrile/styrene copolymers; acrylonitrile/styrene copolymers modified with butadiene/styrene elastomer; cellophane; cyclohexylene dimethylene terephthalate and 1,4-cyclohexylene dimethylene isophthalate copolymers; ethylene-acrylic acid copolymers; ethylene-1,4-cyclohexylene dimethylene terephthalate copolymers; ethylene-ethyl acrylate copolymers; ionomeric resins; ethylene-methyl acrylate copolymer resins; ethylene-vinyl acetate copolymers; ethylene-vinyl acetate-vinyl alcohol copolymers; fluorocarbon resins; hydroxyethyl cellulose film, water-insoluble; isobutylene polymers; isobutylenebutene copolymers; 4,4'-isopropylidenediphenolepichlorohydrin resins; melamine-formaldehyde resins; nitrile rubber modified acrylonitrile-methyl acrylate copolymers; nylon resins; olefin polymers; perfluorocarbon resins; polyarylate resins; polyarylsulfone resins; poly-1-butene resins and butene/ethylene copolymers; polycarbonate resins; polyester elastomers; polyetherimide resins; polyethylene resins, carboxyl modified; polyethylene, chlorinated; polyethylene, fluorinated; polyethylene, oxidized; polyethylene phthalate polymers; poly(p-methylstyrene) and rubber-modified poly(p-methylstyrene); polystyrene and rubber-modified polystyrene; polysulfide polymer-polyepoxy resins; polysulfone resins; poly (tetramethylene terephthalate); polyvinyl alcohol films; polyurethane resins; styrene block polymers; styrene-maleic anhydride copolymers; styrene-methyl methacrylate copolymers; textryls; urea-formaldehyde resins; vinyl chloride-ethylene copolymers; vinyl chloride-hexene-1 copolymers; vinyl chloride-lauryl vinyl ether copolymers; vinyl chloride-propylene copolymers; vinylidene chloride/methyl acrylate copolymers; vinylidene chloride/methyl acrylate/methyl methacrylate polymers; ethylene polymers, chlorosulfonated; 4,4'-isopropylidenediphenol-epichlorohydrin thermosetting epoxy resins; mineral reinforced nylon resins; perflourocarbon cured elastomers; phenolic resins; polyester resins, cross-linked; polyether resins, chlorinated; polyethersulfone resins; polyamide-imide resins; poly(2,6-dimethyl-1,4-phenylene) oxide resins; polyoxymethylene copolymers; polyoxymethylene homopolymers; polyphenylene sulfide resins; polyvinylidene fluoride resins; and styrenedivinylbenzene resins, cross-linked.

12. The composition according to claim 4, wherein the resin is a polymeric material selected from the group consisting of acrylic and modified acrylic plastics; acrylonitrile/butadiene/styrene copolymers; acrylonitrile/butadiene/styrene/methyl methacrylate copolymers; acrylonitrile/styrene copolymers; acrylonitrile/styrene copolymers modified with butadiene/styrene elastomer; cellophane; cyclohexylene dimethylene terephthalate and 1,4-cyclohexylene dimethylene isophthalate copolymers; ethylene-acrylic acid copolymers; ethylene-1,4-cyclohexylene dimethylene terephthalate copolymers; ethylene-ethyl acrylate copolymers; ionomeric resins; ethylene-methyl acrylate copolymer resins; ethylene-vinyl acetate copolymers; ethylene-vinyl acetate-vinyl alcohol copolymers; fluorocarbon resins; hydroxyethyl cellulose film, water-insoluble; isobutylene polymers; isobutylenebutene copolymers; 4,4'-isopropylidenediphenolepichlorohydrin resins; melamine-formaldehyde resins; nitrile rubber modified acrylonitrile-methyl acrylate copolymers; nylon resins; olefin polymers; perfluorocarbon resins; polyarylate resins; polyarylsulfone resins; poly-1-butene resins and butene/ethylene copolymers; polycarbonate resins; polyester elastomers; polyetherimide resins; polyethylene resins, carboxyl modified; polyethylene, chlorinated; polyethylene, fluorinated; polyethylene, oxidized; polyethylene phthalate polymers; poly(p-methylstyrene) and rubber-modified poly(p-methylstyrene); polystyrene and rubber-modified polystyrene; polysulfide polymer-polyepoxy resins; polysulfone resins; poly (tetramethylene terephthalate); polyvinyl alcohol films; polyurethane resins; styrene block polymers; styrene-maleic anhydride copolymers; styrene-methyl methacrylate copolymers; textryls; urea-formaldehyde resins; vinyl chloride-ethylene copolymers; vinyl chloride-hexene-1 copolymers; vinyl chloride-lauryl vinyl ether copolymers; vinyl chloride-propylene copolymers; vinylidene chloride/methyl acrylate copolymers; vinylidene chloride/methyl acrylate/methyl methacrylate polymers; ethylene polymers, chlorosulfonated; 4,4'-isopropylidenediphenol-epichlorohydrin thermosetting epoxy resins; mineral reinforced nylon resins; perflourocarbon cured elastomers; phenolic resins; polyester resins, cross-linked; polyether resins, chlorinated; polyethersulfone resins; polyamide-imide resins; poly(2,6-dimethyl-1,4-phenylene) oxide resins; polyoxymethylene copolymers; polyoxymethylene homopolymers; polyphenylene sulfide resins; polyvinylidene fluoride resins; and styrenedivinylbenzene resins, cross-linked.

13. The composition according to claim 5, wherein the resin is a polymeric material selected from the group consisting of acrylic and modified acrylic plastics; acrylonitrile/butadiene/styrene copolymers; acrylonitrile/butadiene/styrene/methyl methacrylate copolymers; acrylonitrile/styrene copolymers; acrylonitrile/styrene copolymers modified with butadiene/styrene elastomer; cellophane; cyclohexylene dimethylene terephthalate and 1,4-cyclohexylene dimethylene isophthalate copolymers; ethylene-acrylic acid copolymers; ethylene-1,4-cyclohexylene dimethylene terephthalate copolymers; ethylene-ethyl acrylate copolymers; ionomeric resins; ethylene-methyl acrylate copolymer resins; ethylene-vinyl acetate copolymers; ethylene-vinyl acetate-vinyl alcohol copolymers; fluorocarbon resins; hydroxyethyl cellulose film, water-insoluble; isobutylene polymers; isobutylenebutene copolymers; 4,4'-isopropylidenediphenolepichlorohydrin resins; melamine-formaldehyde resins; nitrile rubber modified acrylonitrile-methyl acrylate copolymers; nylon resins; olefin polymers; perfluorocarbon resins; polyarylate resins; polyarylsulfone resins; poly-1-butene resins and butene/ethylene copolymers; polycarbonate resins; polyester elastomers; polyetherimide resins; polyethylene resins, carboxyl modified; polyethylene, chlorinated; polyethylene, fluorinated; polyethylene, oxidized; polyethylene phthalate polymers; poly(p-methylstyrene) and rubber-modified poly(p-methylstyrene); polystyrene and rubber-modified polystyrene; polysulfide polymer-polyepoxy resins; polysulfone resins; poly (tetramethylene terephthalate); polyvinyl alcohol films; polyurethane resins; styrene block polymers; styrene-maleic anhydride copolymers; styrene-methyl methacrylate copolymers; textryls; urea-formaldehyde resins; vinyl chloride-ethylene copolymers; vinyl chloride-hexene-1 copolymers; vinyl chloride-lauryl vinyl ether copolymers; vinyl chloride-propylene copolymers; vinylidene chloride/methyl acrylate copolymers; vinylidene chloride/methyl acrylate/methyl methacrylate polymers; ethylene polymers, chlorosulfonated; 4,4'-isopropylidenediphenol-epichlorohydrin thermosetting epoxy resins; mineral reinforced nylon resins; perflourocarbon cured elastomers; phenolic resins; polyester resins, cross-linked; polyether resins, chlorinated; polyethersulfone resins; polyamide-imide resins; poly(2,6-dimethyl-1,4-phenylene) oxide resins; polyoxymethylene copolymers; polyoxymethylene homopolymers; polyphenylene sulfide resins; polyvinylidene fluoride resins; and styrenedivinylbenzene resins, cross-linked.

14. The composition according to claim 1 wherein the pigment contains about 0.1%–50% by weight of the solvated dye.

15. A method for providing the skin, hair or nails of a person with an attractive cosmetic effect comprising applying to the skin, hair or nails an effective amount of the composition of claim 14.

16. The composition according to claim 1, wherein the composition is in the form of a stick suitable for application to the lips.

17. The composition according to claim 1, wherein the composition is in a powder form.

18. The composition according to claim 1, wherein the composition is in a liquid form.

19. A method for providing the skin, hair or nails of a person with an attractive cosmetic effect comprising applying to the skin, hair or nails an effective amount of the composition of claim 1.

20. A method for providing the skin, hair or nails of a person with an attractive cosmetic effect comprising applying to the skin, hair or nails an effective amount of the composition of claim 2.

21. A method for providing the skin, hair or nails of a person with an attractive cosmetic effect comprising applying to the skin, hair or nails an effective amount of the composition of claim 3.

22. A method for providing the skin, hair or nails of a person with an attractive cosmetic effect comprising applying to the skin, hair or nails an effective amount of the composition of claim 4.

23. A method for providing the skin, hair or nails of a person with an attractive cosmetic effect comprising applying to the skin, hair or nails an effective amount of the composition of claim 5.

24. A method for providing the skin, hair or nails of a person with an attractive cosmetic effect comprising applying to the skin, hair or nails an effective amount of the composition of claim 6.

25. A method for providing the skin, hair or nails of a person with an attractive cosmetic effect comprising applying to the skin, hair or nails, an effective amount of the composition of claim 7.

26. A method for providing the skin, hair or nails of a person with an attractive cosmetic effect comprising applying to the skin, hair or nails, an effective amount of the composition of claim 8.

27. A method for providing the skin, hair or nails of a person with an attractive cosmetic effect comprising applying to the skin, hair or nails, an effective amount of the composition of claim 9.

28. A method for providing the skin, hair or nails of a person with an attractive cosmetic effect comprising applying to the skin, hair or nails, an effective amount of the composition of claim 10.

29. A method for providing the skin, hair or nails of a person with an attractive cosmetic effect comprising applying to the skin, hair or nails an effective amount of the composition of claim 11.

30. A method for providing the skin, hair or nails of a person with an attractive cosmetic effect comprising applying to the skin, hair or nails an effective amount of the composition of claim 12, 31. A method for providing the skin, hair or nails of a person with an attractive cosmetic effect comprising applying to the skin, hair or nails an effective amount of the composition of claim 13.

32. A method for providing the lips of a person with an attractive cosmetic effect comprising applying to the lips an effective amount of the composition of claim 16.

33. A method for providing the skin or hair of a person with an attractive cosmetic effect comprising applying to the skin or hair an effective amount of the composition of claim 17.

34. The method of claim 33 wherein the composition is applied to the cheeks of a person.

35. A method for providing the skin, hair or nails of a person with an attractive cosmetic effect comprising applying to the nails an effective amount of the composition of claim 18.

* * * * *